(12) United States Patent
Berling et al.

(10) Patent No.: US 7,985,743 B1
(45) Date of Patent: Jul. 26, 2011

(54) TOPICAL PAIN RELIEVER AND METHOD OF MAKING THE SAME

(75) Inventors: James M. Berling, Salt Lake City, UT (US); Marion Louise Berling, legal representative, Salt Lake City, UT (US); Gene A. Tabish, Salt Lake City, UT (US)

(73) Assignee: Gene A. Tabish, Salt Lake City, UT (US)

( * ) Notice: Subject to any disclaimer, the term of this patent is extended or adjusted under 35 U.S.C. 154(b) by 1363 days.

(21) Appl. No.: 11/491,528

(22) Filed: Jul. 21, 2006

Related U.S. Application Data

(60) Provisional application No. 60/701,739, filed on Jul. 22, 2005.

(51) Int. Cl.
*A61K 31/60* (2006.01)

(52) U.S. Cl. .......................... 514/159; 514/164; 424/401

(58) Field of Classification Search .................. 424/401; 514/159, 164
See application file for complete search history.

(56) References Cited

U.S. PATENT DOCUMENTS

| | | | |
|---|---|---|---|
| 1,787,924 A | 1/1931 | Whorton | |
| 2,056,208 A | 10/1936 | Putt | |
| 2,095,571 A | 10/1937 | Nichols | |
| 3,119,739 A | 1/1964 | Campbell | |
| 4,199,576 A | 4/1980 | Reller et al. | |
| 4,542,127 A * | 9/1985 | Hitzel et al. | 514/161 |
| 4,975,269 A | 12/1990 | Chavkin et al. | |
| 4,987,133 A * | 1/1991 | Kurmeier et al. | 514/161 |
| 5,223,267 A | 6/1993 | Nichols | |
| 5,736,126 A | 4/1998 | Van Engelen et al. | |
| 5,980,921 A | 11/1999 | Biedermann et al. | |
| 6,001,340 A | 12/1999 | Rosen et al. | |
| 6,156,299 A | 12/2000 | Rosen et al. | |
| 6,416,772 B1 | 7/2002 | Van Engelen et al. | |
| 6,503,488 B1 | 1/2003 | Rosen et al. | |
| 6,703,009 B1 | 3/2004 | Rosen et al. | |

OTHER PUBLICATIONS

Webster's New World Dictionary, Third college Edition. 1988, p. 371.*

\* cited by examiner

*Primary Examiner* — Jennifer M Kim
(74) *Attorney, Agent, or Firm* — Clayton, Howarth & Cannon, P.C.

(57) ABSTRACT

A topical pain reliever and method of making the same is disclosed. The topical pain reliever may comprise effective amounts of water, glycerine, analgesic agent such as salicylic acid or a derivative thereof, and alcohol. The method of making the topical pain reliever may maintain the analgesic agent in suspension within a solution. The topical pain reliever may be applied to the skin of a user to provide pain relief without ingestion of the composition, thereby potentially avoiding adverse side effects.

13 Claims, 2 Drawing Sheets

WATER 64 OZ.

GLYCERINE 32 OZ.

ALCOHOL 32 OZ.

POWDERED ASPIRIN (or other ANALGESIC AGENT) BETWEEN ABOUT 1% AND ABOUT 7%

FIG. 1

(INGREDIENTS)

(METHOD)

US 7,985,743 B1

TOPICAL PAIN RELIEVER AND METHOD OF MAKING THE SAME

CROSS-REFERENCE TO RELATED APPLICATIONS

This application claims the benefit of U.S. Provisional Application No. 60/701,739, filed Jul. 22, 2005, which is hereby incorporated by reference herein in its entirety, including but not limited to those portions that specifically appear hereinafter, the incorporation by reference being made with the following exception: In the event that any portion of the above-referenced provisional application is inconsistent with this application, this application supercedes said above-referenced provisional application.

STATEMENT REGARDING FEDERALLY SPONSORED RESEARCH OR DEVELOPMENT

Not Applicable.

BACKGROUND

1. The Field of the Invention

The present disclosure relates generally to pain relievers, and more particularly, but not necessarily entirely, to a topical pain reliever solution, and method of making the same, that is comprised of both natural and synthetic ingredients.

2. Description of Related Art

It is common practice to provide a topical pain reliever using salicylic acid, aka aspirin, a well-known anti-inflammatory. Aspirin has been used effectively for many years in the medical and scientific community as a pain reliever. Despite its benefits, aspirin has been shown to cause certain side effects in its users, for example stomach irritation and other internal problems associated with ingesting aspirin.

Applying an aspirin solution topically to a user's skin, thereby avoiding the need for a user to ingest aspirin, has been shown to be an effective manner of gaining the benefits of aspirin without the potential side effects. However, there are difficulties associated with the ability to achieve a safe and stable form of a topical pain reliever containing aspirin that will remain in suspension within the solution of the topical pain reliever.

It is an important aspect of any aspirin based topical pain reliever to permeate the necessary layers of the integument or skin in order to relieve pain without adversely affecting vital internal organs. Accordingly, an effective topical pain reliever should be in the form of a solution that dissolves aspirin or other analgesic agents and transports it topically to the area of pain where it can then permeate the integument or skin to provide effective relief. Topical pain relievers in the form of solution have been introduced in the past, but such topical pain relievers have traditionally had problems of maintaining the aspirin or other analgesic in suspension within the solution of the topical pain reliever.

Further, topical pain relievers have been known to take effect long after they have been applied to the integument or skin. Several reasons may cause such a result, for example the topical pain reliever may not effectively permeate the skin, thereby increasing the amount of time for a user to experience any pain relief.

While certain solutions effectively cause the pain relievers to permeate the skin, the pain reliever should remain in suspension within the solution, i.e., should remain stable, such that it has a marketable shelf life. Aspirin is sparingly soluble in water. Permeating solutions may degrade aspirin and other analgesics by a variety of scientific processes including, for example, hydrolysis, glycolysis, and transesterification.

The industry has sought to minimize the effects of the above problems and to maintain a stable solution of aspirin, such as the invention disclosed in U.S. Pat. No. 6,416,772 (Van Engelen et al.). Van Engelen et al. disclose a liquid composition applied transdermally for relief of pain comprising alcohol, glycerin, an analgesic agent such as aspirin or other derivative of salicylic acid, methylsulfonylmethane, and emu oil, which permeates the skin to relieve pain.

The present application discloses a topical pain relieving formula and solution including aspirin or other analgesic agent(s), and an effective method of making the same, which maintains the aspirin or other analgesic agent(s) in suspension within the solution, which has the ability to safely permeate skin and that also has a stable shelf life.

The features and advantages of the disclosure will be set forth in the description that follows, and in part will be apparent from the description, or may be learned by the practice of the disclosure without undue experimentation. The features and advantages of the disclosure may be realized and obtained by means of the formulas and combinations particularly pointed out in the appended claims.

BRIEF DESCRIPTION OF THE DRAWINGS

The features and advantages of the disclosure will become apparent from a consideration of the subsequent detailed description presented in connection with the accompanying drawings in which:

FIG. 1 is a chart illustrating one exemplary embodiment of a formulation of ingredients of a topical pain reliever made in accordance with the principles of the present disclosure.

DETAILED DESCRIPTION

Figure 2:
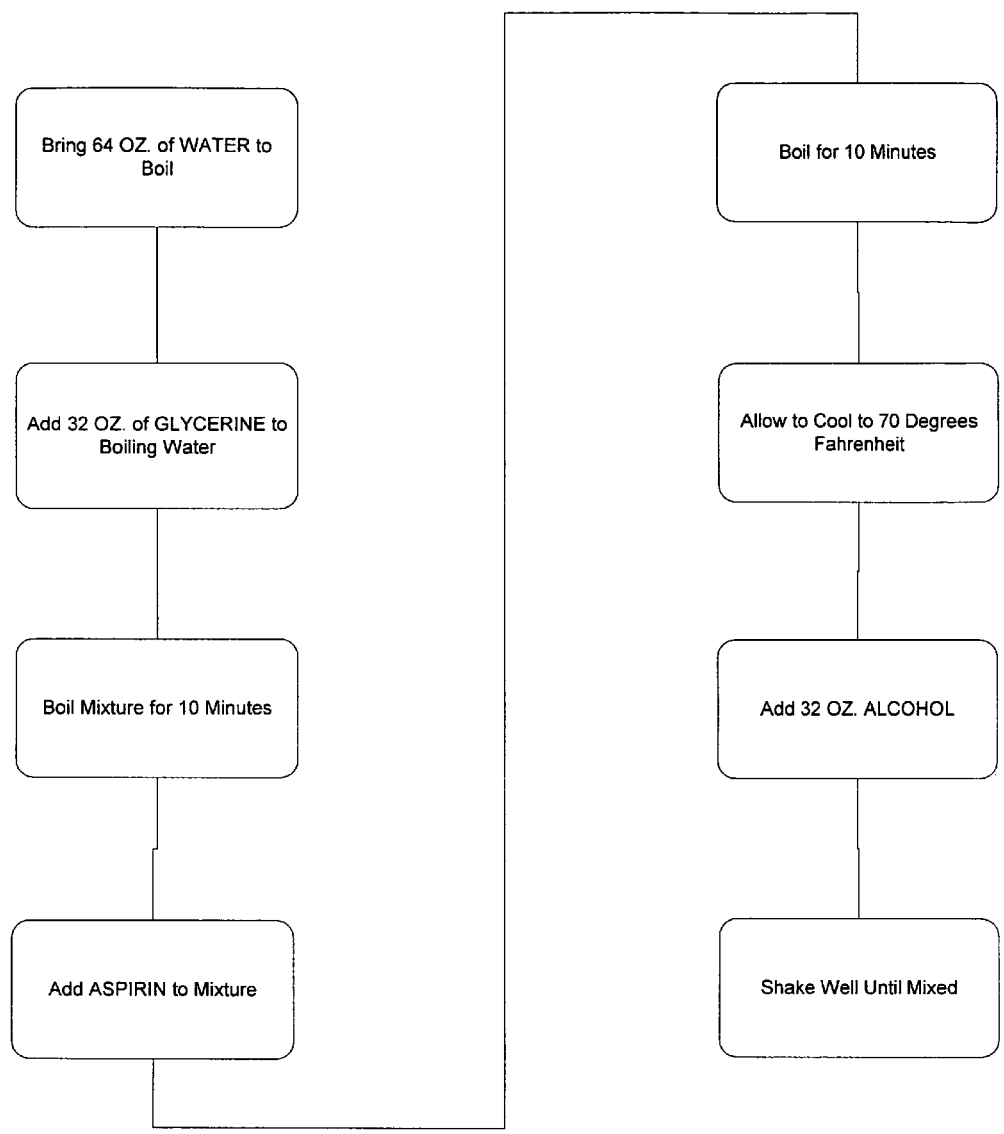
FIG. 2 is a flow chart illustrating a method of preparing or making the topical pain reliever of FIG. 1.

For the purposes of promoting an understanding of the principles in accordance with the disclosure, reference will now be made to the embodiments illustrated in the drawings and specific language will be used to describe the same. It will nevertheless be understood that no limitation of the scope of the disclosure is thereby intended. Any alterations and further modifications of the inventive features illustrated herein, and any additional applications of the principles of the disclosure as illustrated herein, which would normally occur to one skilled in the relevant art and having possession of this disclosure, are to be considered within the scope of the disclosure claimed.

Before the present compositions and methods for making a topical pain reliever are disclosed and described, it is to be understood that this disclosure is not limited to the particular configurations, process steps, ingredients, and materials disclosed herein as such configurations, process steps, ingredients and materials may vary somewhat. It is also to be understood that the terminology employed herein is used for the purpose of describing particular embodiments only and is not intended to be limiting since the scope of the present disclosure will be limited only by the appended claims and equivalents thereof.

The publications and other reference materials referred to herein to describe the background of the disclosure, and to provide additional detail regarding its practice, are hereby incorporated by reference herein in their entireties, with the following exception: In the event that any portion of said reference materials is inconsistent with this application, this application supercedes said reference materials. The reference materials discussed herein are provided solely for their disclosure prior to the filing date of the present application. Nothing herein is to be construed as a suggestion or admission that the inventors are not entitled to antedate such disclosure by virtue of prior disclosure, or to distinguish the present disclosure from the subject matter disclosed in the reference materials.

In describing and claiming the subject matter of the present disclosure, the following terminology will be used in accordance with the definitions set out below.

As used in this specification and the appended claims, the singular forms "a," "an," and "the" include plural referents unless the context clearly dictates otherwise.

As used herein, the terms "comprising," "including," "containing," "characterized by," and grammatical equivalents thereof are inclusive or open-ended terms that do not exclude additional, unrecited elements or method steps.

To the extent used herein, the phrase "consisting of" and grammatical equivalents thereof exclude any element, step, or ingredient not specified in the claim.

To the extent used herein, the phrase "consisting essentially of" and grammatical equivalents thereof limit the scope of a claim to the specified materials or steps and those that do not materially affect the basic and novel characteristic or characteristics of the claimed disclosure.

To the extent used herein, the term "composition" may also be defined as a solution, wherein the composition or solution may be in liquid, solid, or another state.

Applicants have discovered a pain relieving formulation including an analgesic agent such as acetylsalicylic acid (aspirin), or other salicylic acids, and method of making the same that will maintain an effective amount of the analgesic agent in suspension within a solution for use topically on a user's or patient's skin. The ability to maintain the analgesic agent in suspension within a solution has been and continues to be a sought after feature within the medical community. The present application discloses such an ability as described herein below.

The topical pain relieving formulation of the present disclosure comprises several ingredients that comprise a topical pain reliever. Referring now to FIG. 1, an embodiment of the topical pain relieving formulation may comprise the following ingredients water, glycerine, alcohol, and an analgesic agent, such as powdered aspirin (acetylsalicylic acid). It will be appreciated that other types of analgesic agents may be utilized by the present disclosure other than acetylsalicylic acid, such as other salicylic acids, without departing from the spirit or scope of the present disclosure.

FIG. 1 further discloses the relative amount of each ingredient necessary to make one gallon of the topical pain relieving formulation. It will be appreciated that one of ordinary skill in the art may make more or less of the solution by changing the amounts of the ingredients present in the solution by keeping the relationship between ingredients constant. For example, one of ordinary skill in the art may use half as much water as indicated in FIG. 1, and by so doing would decrease the relative amount of glycerine and alcohol by half, while maintaining about 1% to about 7% by weight of aspirin or other analgesic agent.

Further, it is to be understood that volumes of various ranges may be used without departing from the spirit or scope of the present disclosure. Generally, the topical pain relieving formulation may comprise the following ingredients in the following amounts to make one gallon of pain reliever: (1) about 60 oz. to about 68 oz. of water; (2) about 28 oz. to about 36 oz. of glycerine; (3) about 28 oz. to about 36 oz. of alcohol; and (4) powdered aspirin in an amount between about 1% and about 7% by weight. It will be appreciated that the amount of water, glycerine, alcohol and aspirin may be varied between the range given above without departing from the spirit or scope of the present disclosure.

More specifically, the topical pain relieving formulation may comprise the following ingredients in the following amounts to make one gallon of pain reliever: (1) about 64 oz. of water; (2) about 32 oz. of glycerine; (3) about 32 oz. of alcohol; and (4) powdered aspirin in an amount between about 1% and about 7% by weight. It will be appreciated that the amount of aspirin may be varied between the range given above, such that as little as about 1% by weight of aspirin may be present or as much as about 7% by weight of aspirin may be present in the formulation, and all ranges between about 1% and about 7% are meant to fall within the spirit and scope of the present disclosure.

It will be appreciated that the ingredients that may comprise the topical pain relieving formulation may be present in the following relative amounts, namely: (1) about forty-five percent to about fifty-five percent by volume of water; (2) about twenty percent to about thirty percent by volume of glycerine; (3) about twenty percent to about thirty percent by volume of alcohol; and (4) an effective amount of analgesic agent, such as powdered aspirin (acetylsalicylic acid), in the amount of about 1% to about 7% by weight. It is to be understood that the above ranges are merely exemplary of the relative amounts of the ingredients used in the topical pain relieving formulation of the present disclosure, and one of ordinary skill in the art may modify the relative amounts of each ingredient, and such modifications are meant to fall within the scope of the present disclosure. It will be appreciated that the claimed ingredients, as well as their biological equivalents, can be utilized in any amount, which is an effective amount to achieve the desired results, and one of ordinary skill in the art may modify the amounts and such modifications are meant to fall within the scope of the present disclosure.

It will be appreciated that other ingredients may be added to the formulations described above without departing from the spirit or scope of the present disclosure. For example, various enhancements may be made to the solution or product including adding an alternative, such as pleasing, scent or aroma to the solution, such that when the solution is applied to a user's skin, the solution produces a pleasant odor, scent or aroma. Other modifications may also be made to the solution, such as the addition of other analgesic agents beside aspirin to the solution, for example aloe vera, or the addition of a pleasing color to correspond to the scent or aroma that may be associated with the solution. For example, the solution may have a mint or menthol scent added to it and as such a solution having a slight green color to it may be added for providing a potential pleasing color associated with the scent or aroma.

Referring now to FIG. 2, a flow chart illustrates a method of making the topical pain relieving formulation described above and illustrated in FIG. 1, and may be made in accordance with the principles of the present disclosure. Applicants have found that by following the method of making the topical pain relieving formulation disclosed herein below that the analgesic agent, e.g., aspirin, will remain in suspension within the solution that may comprise the topical pain reliever.

An initial step of the process of making the topical pain reliever of the present disclosure may include adding about 64 oz. of water to a container, and exposing the water to heat and bringing the about 64 oz. of water to a boil. Next, about 32 oz. of glycerine may be added to the boiling water, where the resulting mixture may be boiled for about ten (10) minutes. After the mixture has boiled for about ten (10) minutes, powdered aspirin or other analgesic agent may be added to the mixture and brought to a boil. The resulting mixture may again be boiled for about ten (10) minutes. After the mixture has boiled for about ten (10) minutes, the mixture may be allowed to stand and be cooled to a range from about 65° to about 75° Fahrenheit, and specifically about 70° Fahrenheit. At about the time the mixture reaches about 70° Fahrenheit, about 32 oz. of alcohol may be added to the mixture. At this point, the mixture may be shaken until the mixture may be blended well and all ingredients of the mixture blended sufficiently together or until completely mixed.

It will be appreciated that there is potential for other ingredients to be mixed into the composition in addition to those ingredients enumerated above and disclosed in the accompanying figures. However, Applicants have found that the above ingredients may comprise the base formulation of the topical pain reliever disclosed herein.

In accordance with the features and combinations described above, a useful method of preparing or making a topical pain reliever includes the steps of:

(a) boiling about 64 ounces of water;
(b) adding about 32 ounces of glycerine to the boiling water and boiling a mixture thereof for about ten minutes;
(c) adding about 1% to about 7% by weight of an salicylic acid or derivative thereof to the mixture and boiling said mixture for about ten minutes;
(d) cooling the mixture to about seventy degrees Fahrenheit;
(e) adding about 32 ounces of alcohol to the cooled mixture; and
(f) combining the mixture until thoroughly mixed, thereby forming a topical pain reliever solution.

EXAMPLE

The following formulations represent specific illustrative embodiments of the disclosure. These embodiments may be prepared in the manner indicated above by mixing and blending together the stated ingredients so as to result in a finished solution/product with the precise proportions of the components as indicated. The solution/product may then be packaged in a suitable container for distributing and selling. In the following exemplary embodiments, the formulations may comprise the following ingredients in the amounts indicated to make one gallon of solution or product:

| Formulation A | |
|---|---|
| INGREDIENT | AMOUNT PRESENT |
| Water | between about 60 oz.-about 68oz. |
| Glycerine | between about 28 oz.-about 36oz. |
| Alcohol | between about 28 oz.-about 36oz. |
| Aspirin | about 1% to about 7% by weight |

| Formulation B | |
|---|---|
| INGREDIENT | AMOUNT PRESENT |
| Water | between about 60 oz.-about 68 oz. |
| Glycerine | between about 28 oz.-about 36 oz. |
| Alcohol | between about 28 oz.-about 36 oz. |
| Aspirin | about 2% to about 6% by weight |

| Formulation C | |
|---|---|
| INGREDIENT | AMOUNT PRESENT |
| Water | between about 60 oz.-about 68 oz. |
| Glycerine | between about 28 oz.-about 36 oz. |
| Alcohol | between about 28 oz.-about 36 oz. |
| Aspirin | about 2.5% to about 5.5% by weight |

| Formulation D | |
|---|---|
| INGREDIENT | AMOUNT PRESENT |
| Water | between about 60 oz.-about 68 oz. |
| Glycerine | between about 28 oz.-about 36 oz. |
| Alcohol | between about 28oz.-about 36 oz. |
| Aspirin | about 3% to about 5% by weight |

Those having ordinary skill in the relevant art will appreciate the advantages provided by the features of the present disclosure. For example, it is a potential feature of the present disclosure to provide a topical pain reliever and a method of making the same, in which the analgesic agent may be maintained in suspension within the solution. Another potential feature of the present disclosure is, in accordance with one aspect thereof, to provide a topical pain reliever comprising the following ingredients: (1) about 64 oz. of water; (2) about 32 oz. of glycerine; (3) about 1% to about 7% by weight aspirin; and (4) about 32 oz. of alcohol.

Another potential feature of the present disclosure, in accordance with one aspect thereof, is to provide a method of making a topical pain reliever in the following manner: (a) boiling about sixty-four ounces of water; (b) adding about thirty-two ounces of glycerine to the boiling water and boiling a mixture thereof for about ten minutes; (c) adding about 1% to about 7% by weight of an salicylic acid or derivative thereof to the mixture and boiling said mixture for about ten minutes; (d) cooling the mixture to about seventy degrees Fahrenheit; (e) adding about thirty-two ounces of alcohol to the cooled mixture; and (f) combining the mixture until thoroughly mixed, thereby forming a topical pain reliever solution.

In the foregoing Detailed Description, various features of the present disclosure are grouped together in a single embodiment for the purpose of streamlining the disclosure. This method of disclosure is not to be interpreted as reflecting an intention that the claimed disclosure requires more features than are expressly recited in each claim. Rather, as the following claims reflect, inventive aspects lie in less than all features of a single foregoing disclosed embodiment. Thus, the following claims are hereby incorporated into this Detailed Description by this reference, with each claim standing on its own as a separate embodiment of the present disclosure.

It is to be understood that the above-described arrangements are only illustrative of the application of the principles of the present disclosure. Numerous modifications and alternative arrangements may be devised by those skilled in the art without departing from the spirit and scope of the present disclosure and the appended claims are intended to cover such modifications and arrangements. Thus, while the subject matter of the present disclosure has been shown in the drawings and described above with particularity and detail, it will be apparent to those of ordinary skill in the art that numerous modifications, including, but not limited to, variations in amount, ingredients, materials, shape, form, function and manner of operation and use may be made without departing from the principles and concepts set forth herein.

What is claimed is:

1. A method of making a topical pain reliever, including the steps of:
    (a) boiling a predetermined amount of water;
    (b) adding a predetermined amount of glycerine to the boiling water and boiling a mixture thereof for about ten minutes;
    (c) adding about 1% to about 7% by weight of salicylic acid to the mixture and boiling said mixture for about ten minutes;
    (d) cooling the mixture to about sixty-five degrees to about seventy-five degrees Fahrenheit;
    (e) adding a predetermined amount of alcohol to the cooled mixture; and
    (f) combining the mixture until thoroughly mixed, thereby forming a topical pain reliever solution.

2. The method of claim 1, wherein the method further includes the step of adding an ingredient providing a scent or aroma to the mixture prior to thoroughly combining the mixture.

3. The method of claim 2, wherein the method further includes the step of adding a color ingredient to the mixture to thereby provide color to the topical pain reliever.

4. The method of claim 1, wherein step (a) includes boiling about sixty ounces to about sixty-eight ounces of water.

5. The method of claim 4, wherein step (a) further includes about sixty-four ounces of water.

6. The method of claim 1, wherein step (b) includes adding about twenty-eight ounces to about thirty-six ounces of glycerine to the boiling water.

7. The method of claim 6, wherein step (b) further includes adding about thirty-two ounces of glycerine to the boiling water.

8. The method of claim 1, wherein step (c) includes adding about 5% by weight of salicylic acid to the mixture.

9. The method of claim 8, wherein step (c) further includes adding powdered aspirin to the mixture.

10. The method of claim 1, wherein step (d) includes cooling the mixture to about seventy degrees Fahrenheit.

11. The method of claim 1, wherein step (e) includes adding about twenty-eight ounces to about thirty-six ounces of alcohol to the mixture.

12. The method of claim 11, wherein step (e) further includes adding about thirty-two ounces of alcohol to the mixture.

13. A method of making a topical pain reliever, including the steps of:
    (a) boiling about sixty-four ounces of water;
    (b) adding about thirty-two ounces of glycerine to the boiling water and boiling a mixture thereof for about ten minutes;
    (c) adding about 1% to about 7% by weight of salicylic acid to the mixture and boiling said mixture for about ten minutes;
    (d) cooling the mixture to about seventy degrees Fahrenheit;
    (e) adding about thirty-two ounces of alcohol to the cooled mixture; and
    (f) combining the mixture until thoroughly mixed, thereby forming a topical pain reliever solution.

* * * * *